United States Patent [19]
Winters

[11] Patent Number: 5,573,022
[45] Date of Patent: Nov. 12, 1996

[54] ROTATIONALLY ADVANCED DENTAL FLOSS HOLDER AND APPLICATOR ASSEMBLY

[76] Inventor: Steven N. Winters, 2605 E. Commonwealth Ave., Salt Lake City, Utah 84109

[21] Appl. No.: 329,217

[22] Filed: Oct. 26, 1994

[51] Int. Cl.$^6$ .................................................. A61C 15/04
[52] U.S. Cl. ............................................ 132/325; 132/323
[58] Field of Search ...................... 132/321, 322, 132/323, 324, 325, 326, 327, 328

[56] References Cited

U.S. PATENT DOCUMENTS

| | | | |
|---|---|---|---|
| 3,393,687 | 7/1968 | Whitman | 132/323 |
| 3,696,821 | 10/1972 | Adams | 132/324 |
| 3,746,017 | 7/1973 | Casselman | 132/325 |
| 3,833,099 | 9/1974 | Bennington | 132/325 |
| 3,901,251 | 8/1975 | Johnston | 132/326 |
| 3,908,677 | 9/1975 | Beach | 132/325 |
| 4,050,470 | 9/1977 | Miller | 132/323 |
| 4,396,375 | 8/1983 | Gores | 433/141 |
| 4,403,625 | 9/1983 | Sanders et al. | 132/323 |
| 4,926,820 | 5/1990 | Wearn | 132/323 |
| 5,199,452 | 4/1993 | Cheng | 132/323 |
| 5,348,032 | 9/1994 | Mason | 132/325 |
| 5,477,871 | 12/1995 | Sanchez, Jr. | 132/323 |

*Primary Examiner*—David A. Wiecking
*Attorney, Agent, or Firm*—Workman, Nydegger & Seeley

[57] ABSTRACT

A rotationally advanced dental floss holder and applicator assembly that includes a source spool and a take-up spool member to be held in each hand of the user. Dental floss is easily advanced from the source spool member to the take-up spool member by means of rotating the members with the fingers and thereby lessening the time necessary for flossing as well as reducing the amount of dental floss waste. Also disclosed is a dental floss dispenser having a locking mechanism to lock a freely rotating internal spool of dental floss relative to the dental floss dispenser. The locking mechanism is actuated by squeezing the dental floss dispenser and the dental floss dispenser has a finger grip so that the dispenser can be held by the fingers only.

28 Claims, 7 Drawing Sheets

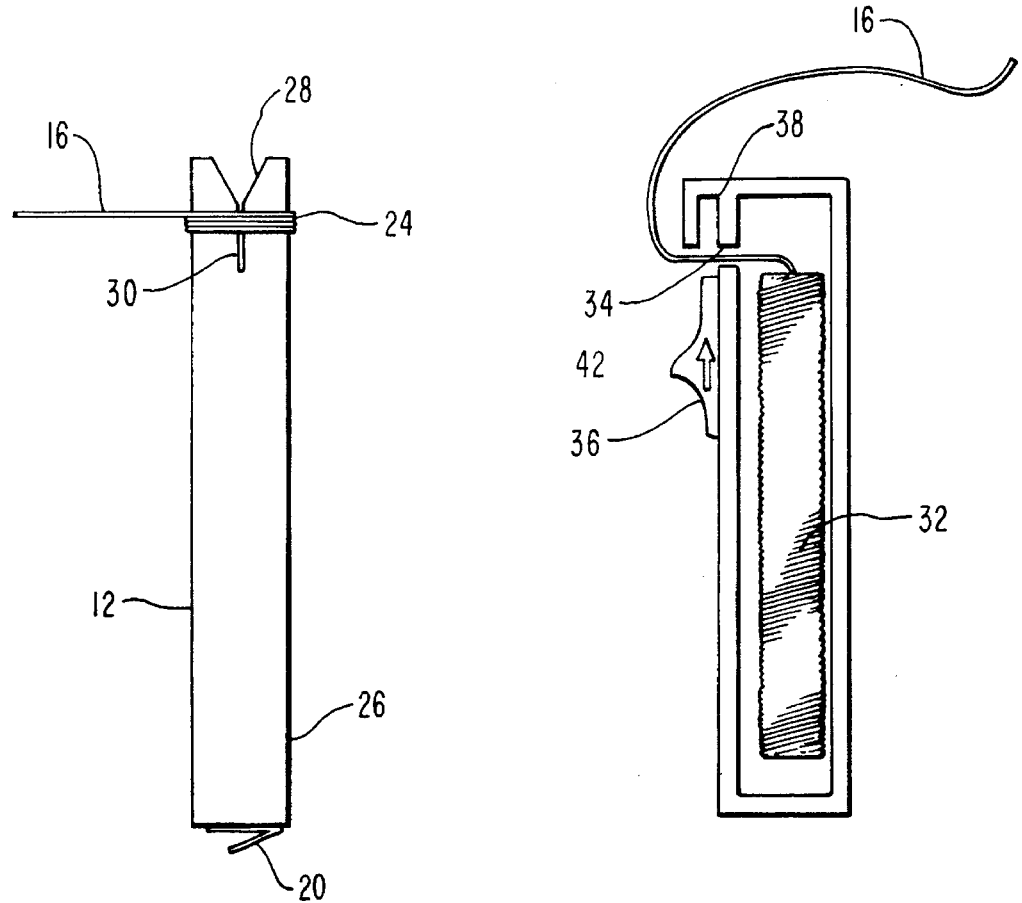
FIG. 3
FIG. 4
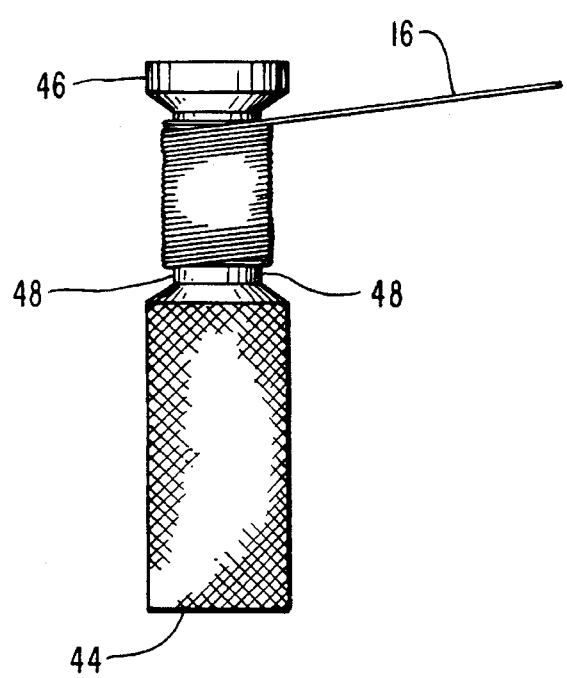
FIG. 5

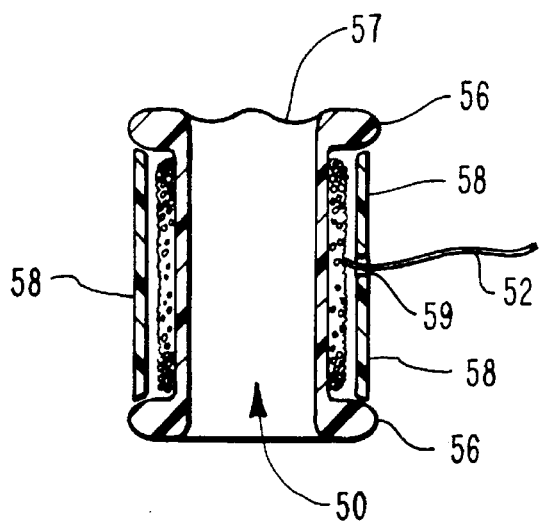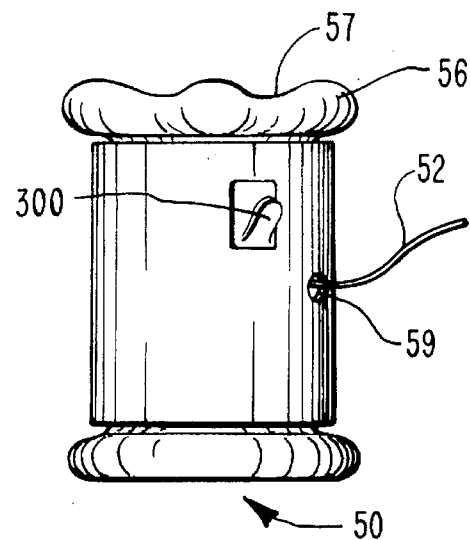
FIG. 8A  FIG. 8B
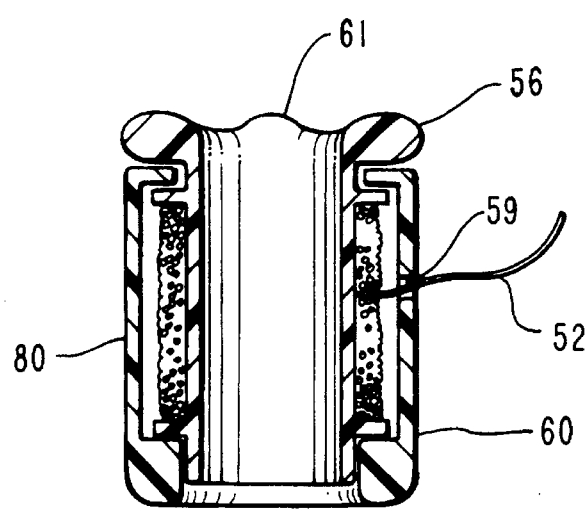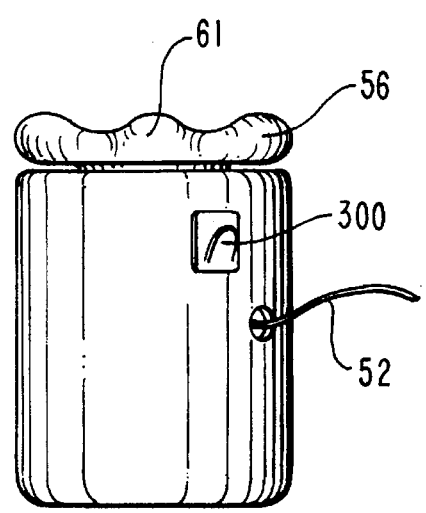
FIG. 9A  FIG. 9B

ROTATIONALLY ADVANCED DENTAL FLOSS HOLDER AND APPLICATOR ASSEMBLY

BACKGROUND OF THE INVENTION

1. Field of the Invention

The present invention relates to tools, assemblies, and apparatus that aid in the dental flossing process and more particularly to those tools or devices that require the use of both hands to operate while leaving the thumb and forefingers free to guide the floss between the teeth or to wipe or brush tooth surfaces. This category of device uses the fingers of the person applying the dental floss to guide and provide the "brushing" action of the dental floss.

2. Description of the Prior Art

Daily flossing has been proven to be an effective and preferred method of oral hygiene when combined with brushing after meals. Some of the benefits that accrue from flossing are healthy teeth and gums, and prevention of tooth decay.

Dentists continuously and vigorously endorse flossing as an integral part of oral hygiene; yet, there continues to be resistance by the public to floss on a regular basis. The process of flossing requires that a strand of dental floss be considerably tensioned and then forced between the teeth. The tensioned floss is then rubbed along the sides of the teeth beneath the gum line thereby using friction to remove plaque. Additionally, food particles and other debris are quickly and easily removed by this action.

Flossing can be done without the aid of tools. This is accomplished by taking a length of dental floss and coiling or wrapping the floss around both index fingers leaving approximately two to four inches between the fingers. With the floss thus coiled, a person may tension the dental floss by pulling the fingers apart. Using the thumb and the index finger, the user may guide the floss to the desired location in her mouth. The index finger and thumb are used to guide the floss in between the teeth. A fair amount of force is necessary to drive the floss in between the teeth.

The forces of keeping the floss tensioned and driving the floss between the teeth tends to cause pain in the index fingers where the dental floss is tightly coiled. A user may even find it necessary to interrupt the flossing process entirely in order to loosen the floss from around the fingers to restore blood flow.

Another common problem is excess waste of dental floss. When wrapping floss around the fingers, a certain excess amount must be used in order to provide enough coils so that the floss will tighten when tensioned. Furthermore, a person is likely to overestimate rather than underestimate the total amount of floss needed.

Yet another problem that is commonly encountered is the awkward nature of advancing the floss so that fresh, unsoiled floss is used against the tooth's surface. A fair amount of disruption occurs when floss is advanced from one finger to the other and then retensioned thus making the floss ready for continued flossing. The overall effect is to increase flossing time, waste floss because of lack of control in how much floss gets advanced, and frustrate the user due to general inconvenience.

Various devices and assemblies have been proposed to overcome these problems of flossing associated with proper dental hygiene. With all of the below mentioned devices, the forefinger and thumb continue to be used to guide and control the tensioned dental floss. While all of them are effective at reducing the pain involved with winding the floss around the forefingers, they have varying degrees of success dealing with the other above-mentioned problems. These devices include U.S. Pat. Nos. 3,393,687 to Whitman, 4,403,625 to Sanders, 3,696,821 to Adams, and 4,050,470 to Miller.

The Whitman applicator provides for one end of the floss to be connected to the applicator while the other end is held by the hand not holding the applicator. Though this applicator effectively may solve the problem of finger pain, it requires a fair amount of effort to thread and set it up for use. Furthermore, the free end of the floss may have to be wrapped or coiled around the finger in order to allow proper tensioning and guidance. Moreover, it does not allow the user to incrementally move the floss strand to get fresh floss without the burdensome process of unthreading and cutting the existing floss strand and then rethreading the applicator with a new strand of floss.

Sanders discloses a disposable hygienic device that acts both as a toothpick as well as a flossing tool. The problem of the pain in the index fingers due to the wrapped floss is solved, but there is no provision for using a continuous strand of floss since the Sanders device is disposable; it is not designed to accommodate new strands of floss. It further fails to incrementally use the floss in a manner that leaves no wasted floss. The effective area of usable floss is relatively small and is likely to become extremely soiled. It also appears that the two pieces that form the handles or the grasping means of the device are very small thereby making it somewhat difficult to grasp.

Adams discloses a pair of thimble like devices to fit over the tops of the index fingers. This allows control and proper tensioning of the floss while protecting the index fingers from painful floss winding. However, moving to a fresh piece of floss is an awkward proposition since one must loosen the thimbles in order to move the floss. Furthermore, the amount of tension created by this method may be less than optimal. It would likewise be wasteful, since users would likely prefer to pull enough floss between the thimbles so that soiled floss is not in contact with the fingers.

Miller discloses an assembly that is used like the present invention with the exception of fresh floss advancement. Finger pain is eliminated but moving the strand of floss in order to place a fresh, unsoiled piece of floss next to the tooth requires disconnecting one of the two members and reconnecting it elsewhere. This is a clumsy process that would be time consuming and wasteful of floss.

None of the previous devices effectively solve the problem in the art of easily transporting a strand of floss such that fresh unsoiled floss can be placed for use in cleaning the teeth. The various ways of repositioning fresh floss in the above-mentioned patents are all unwieldy and hinders the task of flossing the teeth. This in turn makes the chore of daily flossing an oppressive and time consuming operation.

In addition, the above-mentioned ways of advancing the floss tend to be relatively wasteful of the floss. They all leave significant quantities of the floss in a clean and unused condition. The awkwardness of the advancement mechanisms tends to affect the user negatively in that she will tend to continually floss with soiled floss rather than go to the trouble of advancing the floss to get an unsoiled portion of the floss in contact with the teeth thus compromising the quality and effectiveness of the flossing operation.

BRIEF SUMMARY AND OBJECTS OF THE INVENTION

It is an important object of this invention to provide a rotational dental floss holder and applicator assembly consisting of two elongated members; one to be held in each hand. One member contains the source of the dental floss while the second member is a take-up spool for used dental floss. The floss strung between the members provides the proper tension for flossing. The floss may be incrementally advanced by rotating the take-up spool member thereby unwinding floss from the source spool member and doing this without the necessity of retensioning the floss or otherwise significantly interrupting the flossing process.

Furthermore, the elongated source member may be replaced with a simple spool designed to fit around a finger. In this configuration, the user would let the floss rotate freely from the spool when advancing dental floss. The floss is tensioned by bending the finger thus grasping the source spool. The floss on the spool may be exposed or covered by a sleeve.

Furthermore, the source member may be an enhanced version of a standard floss dispenser except it is specifically designed to be held in the palm of the hand during flossing. The dispenser has locking mechanism which is activated when the hand is closed around the dispenser. The closing of the hand causes a member to move against and hold the spool which holds the floss providing the needed tension in the extruding strand of floss. When the hand is opened, the member moves such that the spool is released and the floss can be advanced. Various different means may be used to accomplish the locking action. A number of such means will be explained and others will be apparent to those skilled in the art.

The tightening the hand around the dispenser to produce tension in the strand and the opening of the hand to advance the strand are actions which fit comfortably into the normal flossing procedure. The source dispenser also has slots or gripping means in which fingers are inserted to provide stability when the hand is opened for advancing the floss.

Another important object of the invention is to provide an easy way of advancing the strand of floss. The rotational scheme used whereby floss is rotated from a source spool onto a take-up spool is easily accomplished with the fingertips. The cross-section of the take-up spool can be round or have three or more sides. A square cross-section with only an extremely slight rounding of the edges has proven to be one of the designs which can be easily rotated in the palm using the fingers. It does not necessitate any cumbersome repositioning of the devices or movement of the hands. In this way, total floss time will be shortened and the entire process more enjoyable.

It is a further object of this invention to reduce dental floss waste. Since floss is not wrapped around the index fingers, it is unnecessary to cut off more floss than will be used simply to get the proper tensioning for the flossing process. Secondly, the rotational scheme allows the floss to be advanced incrementally thereby efficiently utilizing nearly the entire quantity of the floss by placing it in direct contact with the teeth to be cleaned at one time or another. Thirdly, the floss can be advanced by an increment equal to the side width of a square rod. If the take-up spool has sides which are a half inch in width, a quarter turn of the rod will only advance the floss a half inch. When floss is directly wrapped around the finger, the only possible advancement length is the diameter of the finger which for adults can be one and one half inches up to two and one half inches. Being forced to advance by such long increments causes a lot of the floss to be unusable.

Yet another object of this invention is to allow the user greater flexibility in choosing the length of working floss. Through being able to increase or decrease the length of working floss by finer increments, the user can continuously alter the length to change the working length and maintain the most comfortable working length while working from the back of the mouth which generally requires longer lengths to the front which requires shorter lengths.

Yet another object of this invention is improved flossing of the teeth. This is accomplished by allowing more new and unused floss to be subjected to the teeth surfaces. Fresh, unsoiled floss is a more effective cleaning tool.

Yet another object of this invention is to reduce the amount of time required for flossing. Using the hand held dispenser and the finger spool the time required for wrapping the floss around a finger is eliminated. As soon as the dispenser is placed in the hand and the floss is inserted in the notch on the take-up spool and the take-up spool is rotated once or twice, the individual is ready to begin flossing. This preparation can be accomplished in less time than the standard process which entails removing the floss from a dispenser, cutting it then wrapping it around both index fingers.

The final object of the invention is to eliminate the pain associated with flossing caused by tightly winding dental floss around the index fingers. Since the means of support for the tensioning is the elongated members or spools, there is no stress on the fingers.

While relatively specific embodiments of the rotational dental floss holder and assembly are disclosed with the accompanying drawings, it will be understood that variations and other assemblies will occur to those skilled in the art.

BRIEF DESCRIPTION OF DRAWINGS

In order that the manner in which the above recited and other advantages and objects of the invention are obtained can be appreciated, a more particular description of the invention briefly described above will be rendered by reference to a specific embodiment which is illustrated in the appended drawings. Understanding that these drawings depict only a typical embodiment of the invention and are not therefore to be considered limiting in scope, the invention will be described and explained with additional specificity and detail through the use of the accompanied drawings in which:

FIG. 3 is a side view of one of the spool members;

FIG. 4 illustrates another embodiment of a source spool member where a spool of dental floss is contained within the member;

FIG. 5 depicts yet another alternate embodiment of a source spool member where a large amount of floss is spooled around the member so the user does not have to load the source spool.

The top of the spool has a waved profile to assist in gripping when the finger is bent.

Figure 6A:
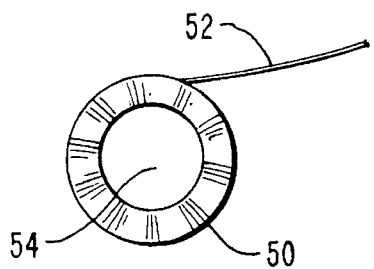
FIG. 6a shows a source spool that is placed on the finger of the user. The rotation or advancement of the floss is controlled by gripping the spool.
Figure 6B:
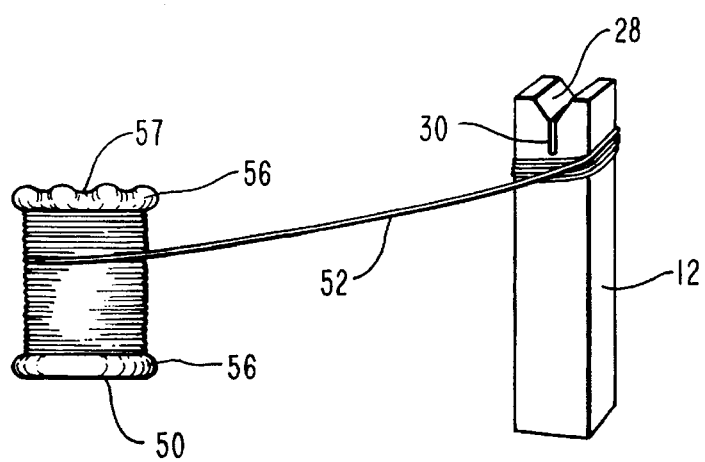

FIG. 6b shows the source spool that is to be placed on a finger in conjunction with a take-up spool.

Figure 7:
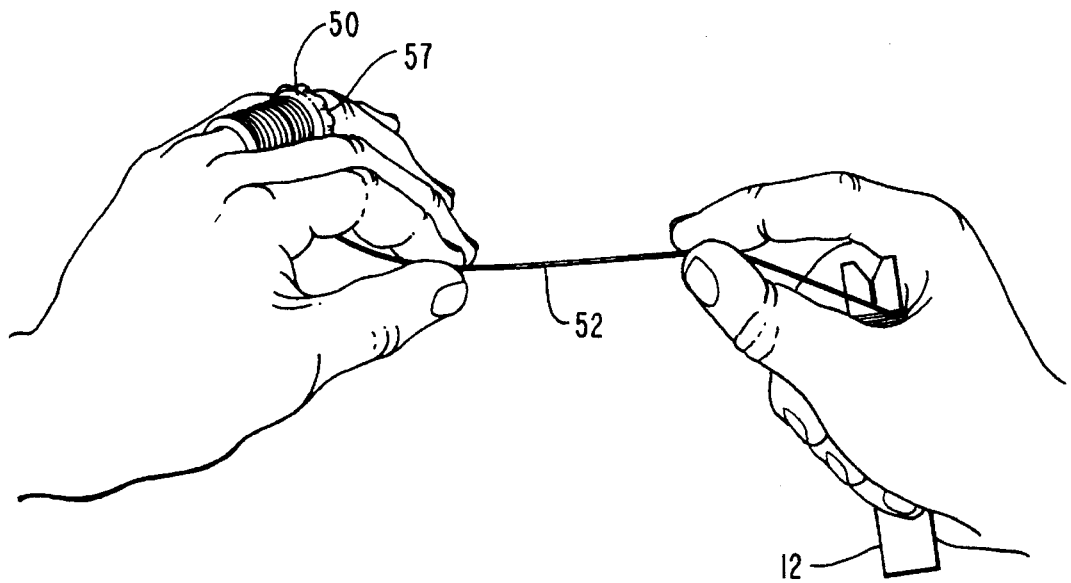

FIG. 7 shows the source spool on the finger of the user and the take-up spool being held in the palm of the other hand.

FIG. 8a shows a cutaway view of the source spool with a freely rotating sleeve covering the floss. The spool rotates on the finger while the sleeve is held in place by the taut strand of floss which extrudes from the hole.

FIG. 8b shows a non-cutaway view of the source spool having a freely rotating sleeve.

FIG. 9a shows a cutaway view of the source spool with a sleeve which rests against the base of the finger. The spool rotates within the sleeve but can still be held by bending the finger and exerting force on the top portion of the spool.

FIG. 9b shows the exterior view of the source spool with a sleeve which rests against the base of the finger.

Figure 10:
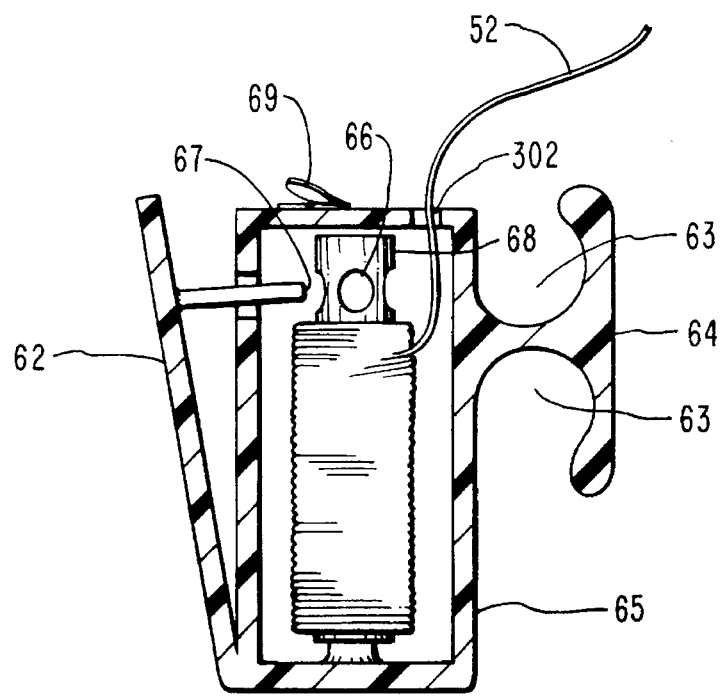

FIG. 10 shows a cutaway view of a source dispenser with the lock in the released position and the portion which holds two fingers when the dispenser is being held.

Figure 11:
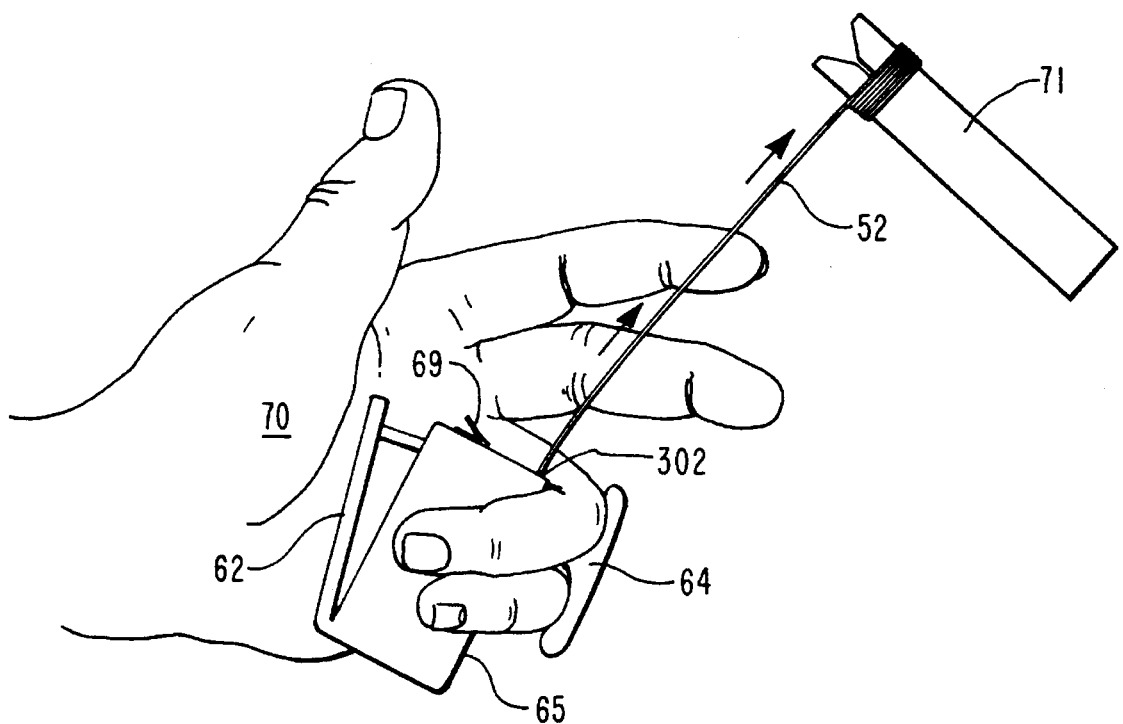

FIG. 11 shows the source dispenser being held in an open hand and, therefore, the dispenser is in the released position and floss can be advanced.

Figure 12:
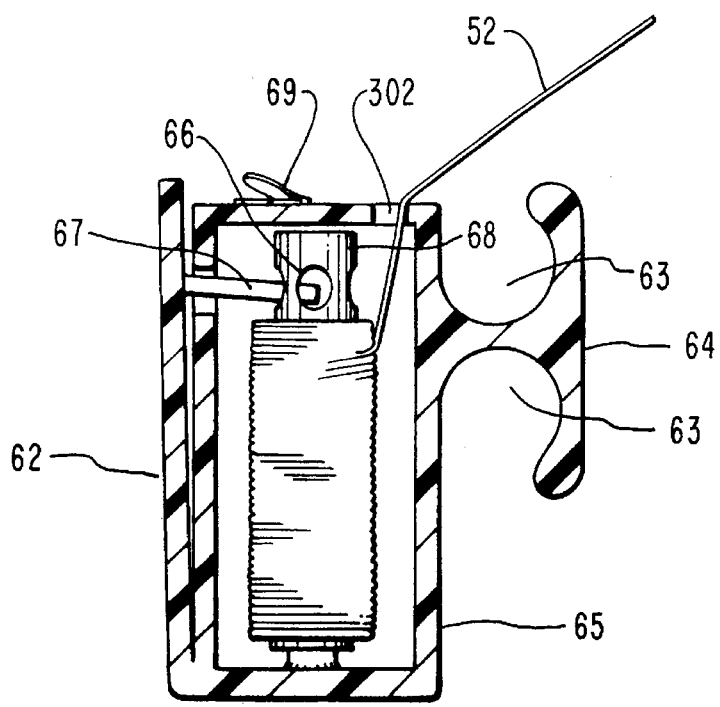

FIG. 12 shows a cutaway view of a source dispenser in the locked position.

Figure 13:
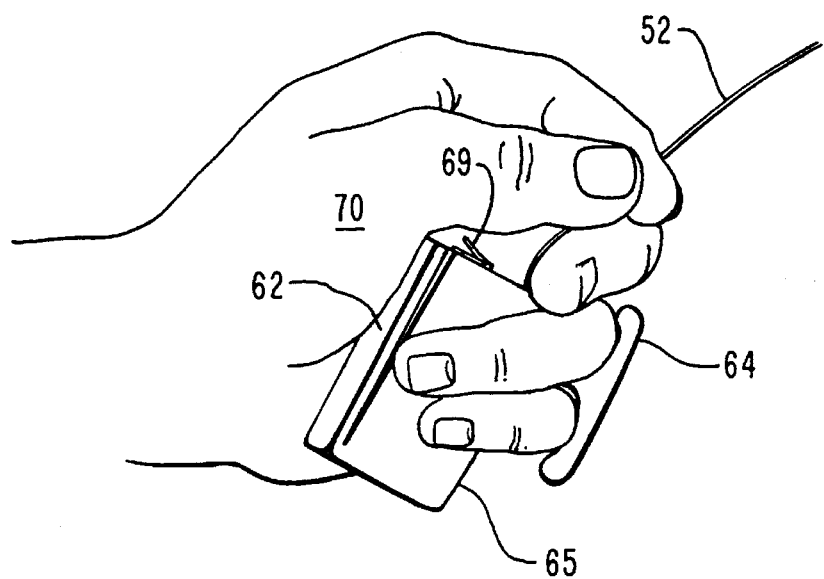

FIG. 13 shows the source dispenser being held in a closed hand and, therefore, the dispenser is in the locked position and floss can be held taught.

Figure 14:
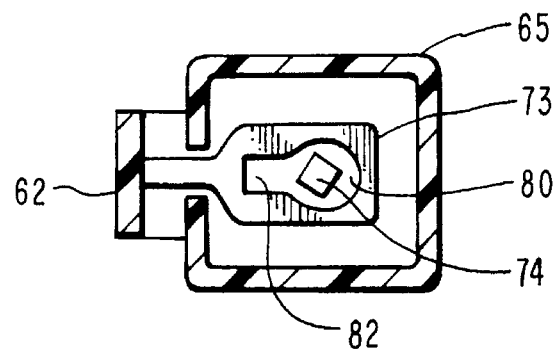

FIG. 14 shows a cross-sectional view of the source dispenser with an alternative locking mechanism with the locking mechanism in the unlocked position.

Figure 15:
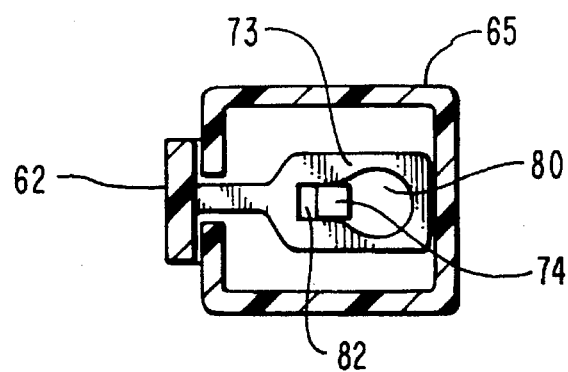

FIG. 15 shows a cross-sectional view of the source dispenser in FIG. 14, but the locking mechanism is in the locked position.

Figure 16:
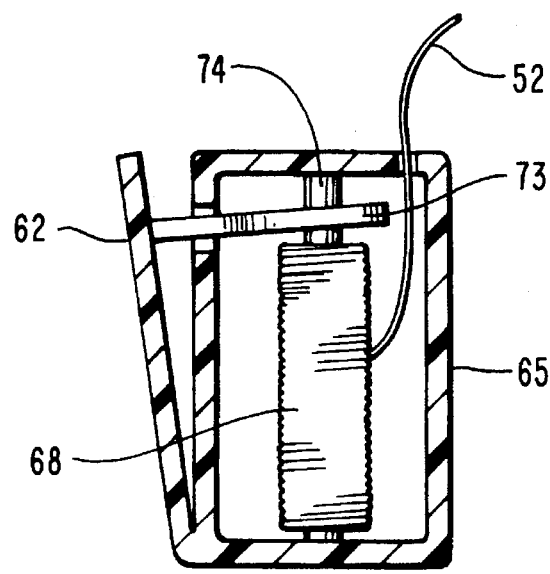

FIG. 16 shows a cutaway view of the source dispenser of FIG. 14 having the alternative locking mechanism.

DESCRIPTION OF THE PREFERRED EMBODIMENT

Figure 1:
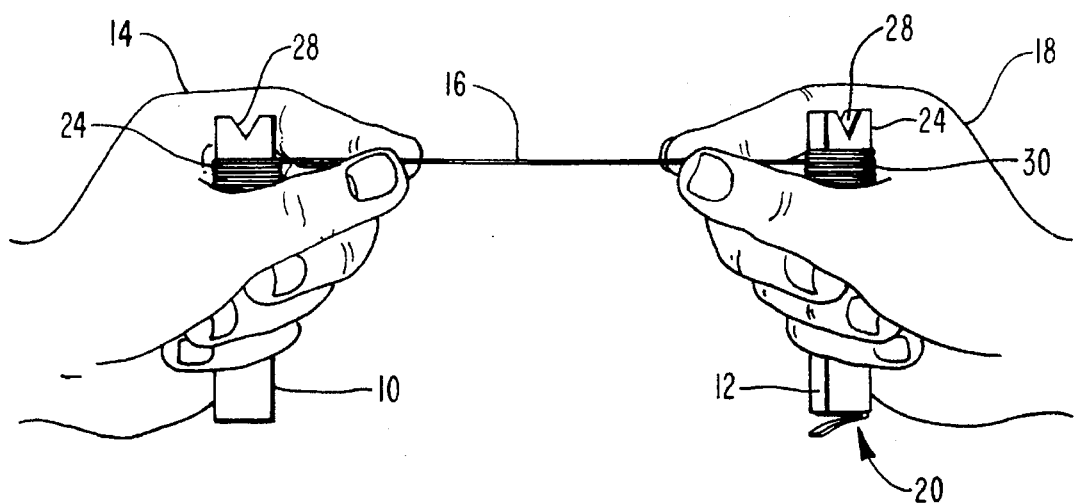
FIG. 1 is a perspective view of the rotational dental floss holder and applicator assembly, illustrating the manner in which an elongated source spool member is grasped by one hand of the user with the dental floss stretched towards the take-up spool member which is held by the other hand of the user during the use thereof with the thumb and index finger of each hand left free to manipulate the floss between the teeth.

The rotational dental floss holder and applicator assembly forming the subject matter of this invention and completely shown in FIG. 1 of the drawings, includes a pair of separate and nearly identical elongated spool members 10 and 12, which members are held apart and contain a strand of dental floss 16 between them to be used for flossing. Furthermore, one member serves as a source spool member 10; being a source of dental floss as it is rotated towards the other member. Likewise, the second member serves as a take-up spool member 12, receiving dental floss from the source spool member as it is rotated therefrom.

The source spool member 10 is held by hand 14 with the lower three fingers of the hand grasped around member 10 while the thumb and index fingers of hand 14 guide the floss 16 while flossing the teeth. Likewise, the take-up spool member 12 is held by hand 18 with the lower three fingers grasping the member 12 and the thumb and forefingers of hand 18 guiding the floss 16.

It is important to realize that the direction of transversal of floss 16 is unimportant. It may go from right to left or from right to left depending on the convenience of the user. In the illustrations, the left hand 14 is pictured holding the source spool member 10 while the dental floss 16 is traversed to the take-up spool member 12 being held by the right hand 18. Again, this is simply illustrative and the spools could be reversed having the floss 16 traverse from left to right with no appreciable change in the invention.

Spool members 10 and 12 are essentially identical with the exception that spool member 12 has a cutting utensil 20 for cutting the floss after use (to discard it). The cutting mechanism 20 could be attached or constructed into either member 10 or 12 at virtually any location. It is shown as an example for convenience during the flossing process.

Take-up spool member 12 is examined in more detail in FIG. 3 and illustrates the functionality and usage of both spool members 10 and 12. Once the rotational dental floss holder and applicator assembly is armed and ready as in FIG. 1, it may be used for flossing teeth. A more particular description of how to arm the rotational dental floss holders and applicator assembly as well as the method of flossing the teeth will be explained in more detail hereinafter.

Figure 2:
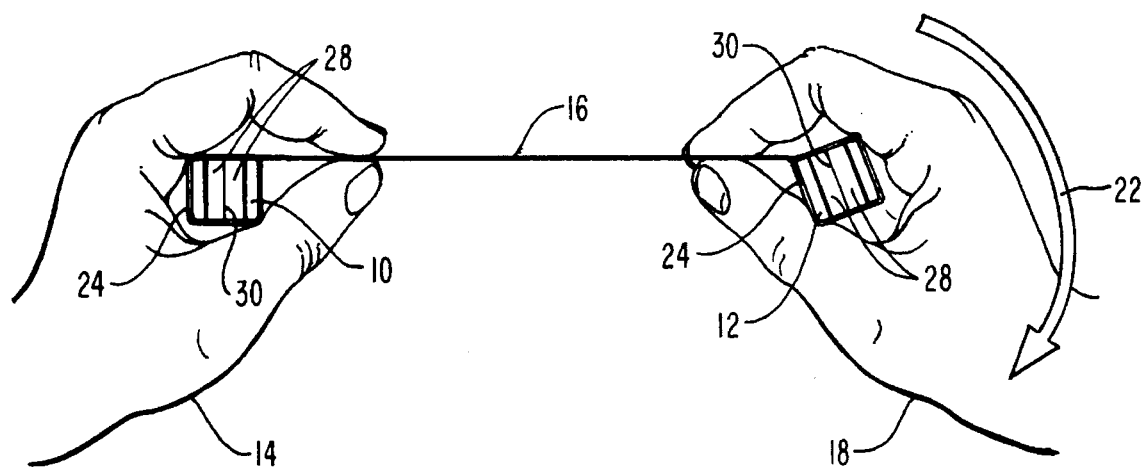
FIG. 2 is a top view of the rotational dental floss holder and applicator assembly showing the rotational motion of the dental floss as it rotates from the source spool member to the take-up spool member.

FIG. 2 illustrates the rotational operation of the two spool members; one being a source spool member 10 the other being a take-up spool member 12. The floss 16 will travel from the source spool member 10 to the take-up spool member 12 as illustrated by the arrow 22. This rotational movement of the floss 16 is accomplished by the fingers of hands 14 and 18, respectively. The hands 14 and 18 rotate the spool members 10 and 12 in order to cause the floss 16 to travel from the source spool member 10 to the take-up spool member 12.

This rotational method of causing the floss 16 to traverse between source spool member 10 and take-up spool member 12 is a major improvement over anything before conceived or suggested regarding hand-held flossing tools and assemblies. It allows fresh areas of the floss to be quickly presented for use in the flossing process. It is easy for the user since only manipulation of the fingers is necessary to get the fresh floss ready for contact with the tooth surface. It does not require cutting the floss or repositioning the tool onto another piece of floss in an unwieldy manner as has been exhibited by devices in the prior art. It further provides for efficient use of the floss since there are not big gaps of unused floss that are discarded in the process of positioning the assembly with the fresh floss.

Dental floss as used in this application refers to the thread-like structure that is commonly purchased for cleaning teeth. It also encompasses variations on this material such as dental tape where the floss may be flattened to create a larger surface to be rubbed against the teeth. The term "dental floss" also encompasses any material that can be used in cleaning teeth that is adaptable to being coiled or spooled around the elongated spool members as shown in the drawings and described in this specification.

FIG. 3 shows a more detailed view of an elongated spool member 12; specifically this would be a take-up spool member 12 as illustrated in FIG. 1. The only difference between this take-up spool member 12 and the source spool member 10 is the cutting device 20 attached to the bottom end 26 of the elongated spool member 12. Additionally, the difference between the source spool member 10 as illustrated in FIG. 1 and a take-up spool member 12 as illustrated in FIG. 1 and FIG. 3 is that the take-up spool member 12 will be receiving used or soiled floss while the source spool member 10 will be giving up fresh or clean floss.

FIG. 3 shows take-up spool member 12 having a bottom end 26 for grasping by the lower three fingers of the hand and a top end 24 containing a means of fastening a length of floss. This is accomplished by a V-shaped opening 28 in the top end 24 of the take-up spool 12. The V-shape opening 28 tapers to a slit 30 that will secure the floss. The purpose of the V-shaped opening 28 is to channel the floss into the slit 30. When the floss 16 is forced into slit 30, the sides of the slit 30 exert sufficient force upon the floss 16 that is securely anchored.

To arm the rotational dental floss holder and applicator assembly, a length of floss 16 sufficient to floss all of the teeth is cut or otherwise removed from a commercially available standard roll of dental floss. One end of the floss 16 is slid through the V-shaped opening 28 of the top end 24 of the source spool member 10. Once the end of the floss 16 is firmly lodged in the slit 30, the floss 16 is wrapped around the top end 24 of the source spool 10. Once spooled, all of the floss 16 is wrapped around the top end 24 of the source spool 10.

The free end of the floss 16 that has been coiled around the top end 24 of the source spool member 10 is taken and slid down the V-shaped opening 28 on the top end 24 of the take-up spool 12. It is lodged firmly in the slit 30 of the top end 24 of the take-up spool 12. With the hand 14 grasping the source spool 10 and the hand 18 grasping the take-up spool 12 the fingers of both hands rotate the respective spool members 10 and 12 until the floss 16 has traversed from source spool member 10 to take-up member 12 and has coiled a few coils around the top end 24 of take-up spool 12.

The floss 16 is tensioned by the user pulling the spool members 10 and 12 away from each other until the desired tension is attained. The forefinger and thumb of hands 14 and 18 are used to guide the tensioned floss 16 into the interproximal spaces between the teeth. The floss 16 can then be rubbed against the side tooth surface or be used to dislodge food particles between the teeth. It can also be used to reach below the gum line as commonly taught by dentists. The fingers of the hands 14 and 18 are free from the pain associated with floss wound around the index finger and better guidance is provided since the floss is tensioned with the spool members 10 and 12.

As a tooth is cleaned and the floss 16 becomes soiled the user may use the hands 14 and 18 to rotate spool members 10 and 12 in such a manner that the floss 16 leaves the source spool member 10 and is taken up or coiled around the take-up spool member 12. This provides fresh floss and hence better cleaning of teeth surfaces.

When flossing is complete, cutting member 20 may be used to sever floss 16 at a point where only fresh floss remains. The soiled floss is then unraveled or uncoiled from the top end 24 of the take-up spool member 12 and discarded.

Those skilled in the art will notice various aids and improvements that can be made on this most basic mode as has been described. For example, texturing may also be placed on the spool members 10 and 12 to provide a firmer grip. Spool members 10 and 12 may also be contoured to provide a more sure grip as well. A little "lip" may be placed at the top of spool members 10 and 12 such that the floss will not slip off the spool members when the spool members 10 and 12 are moved in a downward fashion.

The fastening or securing means illustrated by the shaped opening 28 and the slit 30 are only representative of a simple way of securing the floss 16 for tensioning. This means for fastening the floss to a spool member may be accomplished in a number of ways including but not limited to a clasp, tying it in a knot around the spool member, gluing it, etc. Furthermore, many other ways may become apparent to those skilled in the art. In a simple implementation, the floss may be wound around the member, relying upon the friction of the floss wound upon itself to keep it secure.

The cutting means 20 is simply a punched metal article creating a sharp edge that is attached to the bottom of a take-up spool member 12. It is similar to the cutting means supplied in a common dental floss dispenser, and could alternatively be attached to the bottom of the source spool member 10. It could also be attached in a different area rather than the bottom. Furthermore, the cutting means could be a number of different means besides the punched metal mechanism illustrated. For example, a rough edge on a spool member 10 or 12 could be used to accomplish cutting.

FIG. 4 shows an alternate embodiment of a source spool member 10. FIG. 4 discloses the source spool 40, an internal spool of dental floss 32, a floss exit outlet 34, a sliding switch 36 and a locking switch receptacle 38. A supply of dental floss 16 is held on the internal spool 32 for use with the source spool member embodiment 40. The floss 16 exits the floss exit outlet 34 according to the amount needed for proper flossing. The sliding switch 36 has an open position as shown and a closed position as shown by sliding the switch in the direction of arrow 42. When in the closed position the switch will be firmly placed in the locking receptacle 38 thereby pinching the floss 16. This will provide the fastening means so that the floss 16 may be properly tensioned.

A user would use the fingers of her hand 14 to control the sliding switch 36. When fresh floss is needed the user would slide switch 36 to the open position thereby letting the floss 16 freely travel through the floss outlet 34. The hand 18 would rotate the take-up spool member 12 thereby pulling the floss through outlet 34 from the internal spool 32. Once the floss 16 is properly advanced, the user would use the fingers of hand 14 to close or secure switch 36 into the locking receptacle 38. The floss 16 will then be pinched between the switch and the locking receptacle providing the fastening means for the source spool member 40.

The advantage to the embodiment of the source spool member 40 illustrated in FIG. 4 is that a larger amount of dental floss may be contained on the internal spool 32. It can be commercially prepackaged as an alternative to the standard dental floss dispensers now commonly available. It is important to note that floss may simply be packaged inside the source spool member 40 without the internal spool 32.

Using the switching mechanism may be easier for some users rather than manually rotating the source spool member. For example, those with arthritis may appreciate the ease of simply loosening and tightening the sliding switch 36. Moreover, one could envision complex and motorized spool members on both the take-up and/or source spool members. Other variations would include any freely rotatable spool, internal or external along with a way to secure the floss for tensioning.

Yet another alternative for a source spool member is illustrated in FIG. 5. The source spool member 44 is readily adapted for manufacture and represents a prewound source spool member. A large amount of floss 16 is wrapped around the top end 46 of the source spool member 44. The recessed area 48 can be adjusted to accommodate a desired amount of floss to be prewound around the source spool member 44. The end of the floss 16 will be fastened in a commonly used way. For example, it may be stapled to, glued to, molded into, or otherwise attached to the source spool 44. When the dental floss 16 has been totally used from source spool 44 it can be simply discarded.

The source spool member 44 of FIG. 5 is to used with the take-up spool member 12 of FIG. 3. This allows the user: (1) to load the take-up spool member 12, (2) floss the teeth, (3) use the rotational method of causing the floss 16 to travel from the source spool member to the take-up spool member, (4) cut the used floss from the source spool member 44, and (5) discard the used floss by unwinding the floss that had been captured by the take-up spool member 12.

The advantage of the source spool member 44 of FIG. 5 is that it is easily and inexpensively adapted for manufacture. It provides an easy mechanism for selling dental floss in this preloaded source spool member. This provides further convenience to the user and greatly enhances the probability that flossing will be done on a regular basis.

It may be noted that the prewound source spool member 44 is simply illustrative and that those skilled in the art will clearly devise other aesthetically pleasing designs but that will encompass the same principal of having dental floss wrapped around an elongated source spool member that can be used as shown in FIG. 1. Additional structure may be added to the source spool member 44 of FIG. 5 that would keep the floss enclosed and protected from the external environment.

FIGS. 6a, 6b, and 7 show a spool that may be placed around a finger, preferably the ring finger, thereby serving as a source spool of dental floss. The spool 50 has wrapped around it dental floss 52. The spool 50 has a hollow area 54 for placing the spool around one of the fingers of the hand; preferably the ring finger. When the user desires to advance floss, she loosens the finger and allows the spool to rotate freely around the finger thereby advancing the floss. When the user desires to tension the floss, she merely bends the finger around the spool thereby holding it in a fixed position. The source spool 50 may or may not have flanges 56 to guide and control the floss. The source spool 58 may or may not have waved pattern 57 around the top flange to aid in gripping the spool when the finger is bent. This embodiment of a mere spool around a finger, as shown in FIGS. 6a, 6b, and 7, provides the advantage being easily adapted for manufacture and allows for the personal preference of the user. Some users will find this spool more comfortable than grasping an elongated member.

FIGS. 8a and 8b show the spool 58 of FIGS. 6a, and 7, with a sleeve 58 covering the floss. The sleeve completely covers the floss and can rotate freely around the spool. The floss 52 passes through the sleeve by means of a hole 59 on the sleeve. During use, the tension of floss causes the sleeve to rotate around the spool as floss is dispensed. A punched metal floss cutter 300 may be placed on the sleeve 58.

FIGS. 9a and 9b show a spool 61 with only a top flange 56. The sleeve 60 rests against the base of the finger and does not rotate. When the finger is loosened, the spool 61 rotates within the sleeve 60 thus dispensing floss 52 through the hole 59 in the sleeve. A punched metal floss cutter 300 may be placed on the sleeve 60.

FIG. 10 shows a floss dispenser 65 which is held in the hand during flossing. The dispenser has a locking member 62 which can be pressed such that it prevents the internal spool 68 of floss 52 from rotating. There are several possible locking mechanisms that can be used and the various examples shown here are illustrative. Many others will be apparent to those skilled in the art and are considered within the scope of the present invention.

FIG. 10 shows the locking member 62 with an attached rod 64 which is positioned such that when the locking member 62 is pressed towards the dispenser 65, the rod 64 moves into one of the holes 67 at the top of the spool 68. This locks the spool preventing it from rotating allowing the floss 52 to be pulled to an appropriate working tension. During flossing, two fingers are inserted in the grip area 63 created by a finger grip member 64. The finger grip member 64 holds the fingers firmly in place allowing the user to open his hand to unlock the floss without loosening his grip on the dispenser 65. The dispenser 65 may also have a dental floss cutter 69.

FIG. 11 shows the hand-held floss dispenser 65 being held in an open hand 70. The locking member 62 is not pressed inward so the floss 52 can be advanced by the take-up spool 71. The finger grip member 64 securely holds the two fingers during the process.

FIG. 12 shows the dispenser in the locked position with the locking member 62 being pressed towards the dispenser 65 thus locking the spool 68 by inserting the rod 67 in the hole 68.

The dispenser 65 is in the locked position in FIG. 13 with the hand 70 pressing against the lock member actuator 62.

FIG. 14 shows an alternative method for locking the spool. The lock member actuator 62 is pushed in when the hand is closed. The lock member 73 which locks the spool has a round hole 80 which connects to a square slot 82. The spool 68 has a square cross-sectional spool top 74 designed to fit tightly into the square slot 82 of the lock member 73. The spool 68 may have a cross-sectional top 74 in a shape other than a square. For example, a hexagon, octagon, or any other shape having multiple parallel sides that would fit securely in square slot 82 of lock member 73 would be effective. The more parallel sides on the cross-section top 74, the finer length the floss 52 may be advanced.

When the lock member actuator 62 is not depressed, the spool rotates freely in the circular hole 80. When it is pressed, the spool top 74 locks in the square slot 82 of the lock member 73.

In FIG. 15 the spool 68 is locked by having the spool top 74 securely fitted into the square slot 82 of the lock member 73.

FIG. 16 is a cutaway view of a dispenser 65 having an alternative locking mechanism as more specifically shown in FIGS. 14 and 15.

Yet another way of locking dental floss in a dispenser for proper tensioning is by having the dispenser be made of a squeezable material. As the user compresses the dispenser body, the interior side of the dispenser would come in contact with a freely rotating internal spool of dental floss. As pressure is applied, the spool of dental floss will become locked in a relative position with respect to the squeezable dispenser casing. Once again, many different ways of locking the dental floss will be apparent to those skilled in the art.

The base aspect of all sources of dental floss, whether they be elongated members or spools or variations thereof, is that they provide dental floss that can be readily taken up by the take-up spool member. Furthermore, they must provide a way to tighten or tension the floss so that the floss may be tensioned and proper flossing take place.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A hand-held dental floss dispenser held in one hand for feeding dental floss to the other hand or a take-up member held in the other hand and providing an anchor for tensioning the floss during flossing, the dental floss dispenser comprising:

(a) a dispenser body capable of being gripped by at least one of the lower fingers of the hand leaving the remaining fingers free to manipulate the floss during flossing;

(b) a freely rotatable spool of dental floss rotatably attached to the dispenser body and capable of being locked;

(c) a locking means to lock the freely rotatable spool to a relative position to the dispenser base thereby allowing the dental floss to be tensioned between the dental floss dispenser and the other hand or take-up member held in the other hand.

2. A dental floss dispenser as in claim 1 wherein the freely rotatable spool of dental floss is internal to the dispenser body and has a top end.

3. A dental floss dispenser as in claim 2 wherein the locking means is actuated by squeezing the dispenser body with the lower three fingers and palm of the hand.

4. A dental floss dispenser as in claim 3 wherein the dispenser body is made of squeezable material and the dispenser body has an internal surface capable of frictionally engaging the freely rotatable spool of dental floss and the locking means comprises squeezing the dispenser body until the internal surface of the dispenser body sufficiently engages the freely rotatable spool of dental floss that it is locked in a relative position.

5. A dental floss dispenser as in claim 3 wherein the dispenser body further comprises finger gripping means that allow the dispenser body to be held by the lower three fingers of the hand away from the palm of the hand.

6. A dental floss dispenser as in claim 5 wherein the top end of the freely rotatable spool has locking holes and the locking means further comprises:

(a) a locking member attached external to the dispenser body; and (b) a rod for insertion into the locking holes that is attached to the locking member and passes through the dispenser body to lockingly engage the locking holes.

7. A dental floss dispenser as in claim 5 wherein top end of the freely rotatable spool has multiple parallel sides and the locking means further comprises:

(a) a locking member attached external to the dispenser body; and (b) a slot member attached to the locking member and passing through the dispenser body; having a circular bore adapted for allowing the freely rotatable spool to freely rotate and having a slot immediately connected to the bore and the slot capable of tightly engaging any two of the parallel sides of the top end of the freely rotating spool such that when so engaged the freely rotating spool is locked in relative position to the dispenser body.

8. A rotationally advanced dental floss holder and applicator assembly comprising:

(a) an elongated dental floss source spool member adapted for manual, hand-held rotation, such that the thumb and index finger are free, and including a first dental floss securing means at one end; and (b) an elongated dental floss take-up spool member adapted for manual, hand-held rotation, such that the thumb and index finger are free, and including a second dental floss securing means at one end; wherein one end of the dental floss is secured to the first spool member by the first dental floss securing means and the other end of the dental floss is secured to the take-up spool member by the second dental floss securing means.

9. An incrementally advancable dental floss holder and applicator assembly comprising:

(a) a hand-held dental floss supply source capable of tensioning and feeding dental floss; and (b) an elongated dental floss take-up member having a lower end adapted to being grasped by at least one of the lower three fingers of the hand and an upper end, the upper end having a dental floss securing means wherein a length of dental floss is stored as part of the supply source, extends from the supply source to the take-up member, and is advanced in an incremental fashion from the supply source to the take-up member to be stored entirely on the take-up member until flossing is completed.

10. An assembly as in claim 9 wherein the dental floss supply source comprises a finger spool of dental floss for placement around a finger.

11. An assembly as in claim 10 wherein the finger spool has a waved pattern for better gripping by the hand.

12. An assembly as in claim 10 wherein the finger spool has rotatably attached a freely rotating protective sleeve and the floss is dispensed through a hole in the protective sleeve.

13. An assembly as in claim 10 wherein the finger spool has a sleeve that abuts the base of the finger of the user and the floss is dispensed through a hole in the sleeve.

14. An assembly as in claim 9 wherein the dental floss supply source comprises an elongated dental floss source supply member having a lower end adapted to being grasped by the lower three fingers of the hand, a dental floss storage means, and a dental floss securing means.

15. An assembly as in claim 14 wherein the take-up member dental floss securing means comprises a slit in the take-up member upper end to secure the floss within which the dental floss is compressionally held.

16. An assembly as in claim 15 wherein the source supply member dental floss storage means comprises a length of dental floss wound around the source supply member.

17. An assembly as in claim 15 wherein the source supply member dental floss storage means comprises a length of dental floss wound around a freely rotating spool within the source supply member.

18. An assembly as in claim 15 wherein the source supply member dental floss storage means comprises a length of dental floss wound around a spool rotationally attached to the source supply member.

19. An assembly as in claim 15 wherein the source supply member dental floss storage means comprises a length of dental floss placed inside the source supply member.

20. An assembly as in claim 14 wherein the source supply member dental floss securing means comprises a slit in the source member upper end to secure the floss within which the dental floss is compressionally held.

21. An assembly as in claim 10 wherein the take-up member dental floss securing means comprises a slit in the source member upper end to secure, the floss within which the dental floss is compressionally held.

22. An assembly as in claim 17 wherein the source supply member dental floss securing means comprises:

(a) a sliding switch, and (b) a switch receptacle to receive the sliding switch so that the dental floss is secured between the sliding switch and the switch receptacle.

23. An assembly as in claim 14 wherein the source supply member dental floss securing means comprises:
  (a) a sliding switch, and
  (b) a switch receptacle to receive the sliding switch so that the dental floss is secured between the sliding switch and the switch receptacle.

24. A method of incrementally advancing dental floss comprising the steps of:
  (a) arming an elongated source supply member held in one hand with a length of dental floss having a first end and second end;
  (b) extending the dental floss from the source supply member to a take-up member held in the opposite hand of the hand holding the source supply member;
  (c) securing the second end of the dental floss to the distal end of the take-up member; and
  (d) advancing the dental floss from the source supply member to the take-up member to be stored entirely on the take-up member until flossing is completed.

25. A method as in claim 24 wherein the arming further comprises the steps of:
  (a) securing the first end of the dental floss to the source supply member and
  (b) winding the dental floss around the source supply member.

26. A method as in claim 25 wherein the dental floss is incrementally advanced from the source supply member to the take-up member by manually rotating the source supply member and the take-up member.

27. A method as in claim 24 wherein the arming further comprises the steps of:
  (a) winding the dental floss around a freely rotating spool and
  (b) securing the dental floss with a sliding switch and switch receptacle assembly that pinches and secures the dental floss.

28. A method as in claim 27 wherein the dental floss is incrementally advanced from the source supply member to the take-up member by manually rotating the take-up member.

* * * * *